(12) United States Patent
Chen et al.

(10) Patent No.: US 10,961,515 B1
(45) Date of Patent: Mar. 30, 2021

(54) CARBONYL REDUCTASE VARIANT AND ITS USE IN PREPARATION OF (R)-4-CHLORO-3-HYDROXYBUTYRATE

(71) Applicant: Fudan University, Shanghai (CN)

(72) Inventors: Fener Chen, Shanghai (CN); Zedu Huang, Shanghai (CN); Zexu Wang, Shanghai (CN); Minjie Liu, Shanghai (CN)

(73) Assignee: Fudan University, Shanghai (CN)

( * ) Notice: Subject to any disclaimer, the term of this patent is extended or adjusted under 35 U.S.C. 154(b) by 0 days.

(21) Appl. No.: 16/904,450

(22) Filed: Jun. 17, 2020

(30) Foreign Application Priority Data

Feb. 26, 2020 (CN) .......................... 202010121015.9

(51) Int. Cl.
| | | |
|---|---|---|
| *C12N 9/04* | (2006.01) | |
| *C12N 1/20* | (2006.01) | |
| *C12N 15/52* | (2006.01) | |
| *C12N 15/70* | (2006.01) | |
| *C12N 15/74* | (2006.01) | |
| *C12P 7/62* | (2006.01) | |

(52) U.S. Cl.
CPC ............. *C12N 9/0006* (2013.01); *C12N 1/20* (2013.01); *C12N 15/52* (2013.01); *C12N 15/70* (2013.01); *C12N 15/74* (2013.01); *C12P 7/62* (2013.01); *C12Y 101/01184* (2013.01)

(58) Field of Classification Search
None
See application file for complete search history.

(56) References Cited

FOREIGN PATENT DOCUMENTS

| CN | 104099305 A | 10/2014 |
| CN | 108728421 A | 11/2018 |
| CN | 110551701 A | 12/2019 |

OTHER PUBLICATIONS

Gen Bank Accession No. PTN18108.1, published Apr. 9, 2018 (Year: 2018).*
Park et al., "Enantioselective bioconversion using *Escherichia coli* cells expressing *Saccharomyces cerevisiae* reductase and Bacillus subtilis glucose dehydrogenase", Journal of Microbiology and Biotechnology, vol. 20, No. 9, pp. 1300-1306, 2010 (Year: 2010).*
Ema et al., "Asymmetric reduction of ketones using recombinant *E. coli* cells that produce a versatile carbonyl reductase with high enantioselectivity and broad substrate specificity", Tetrahedron, vol. 62, pp. 6143-6149, 2006 (Year: 2006).*

* cited by examiner

*Primary Examiner* — Richard C Ekstrom

(57) ABSTRACT

Disclosed herein are a carbonyl reductase variant and its use in the preparation of (R)-4-chloro-3-hydroxybutyrate. The carbonyl reductase variant is obtained by mutating phenylalanine-85 in an amino acid sequence as shown in SEQ ID NO:4 to methionine. An amino acid or amino acids at one or more positions other than position 85 in the amino acid sequence of the carbonyl reductase may be further replaced. The application also provides a recombinant expression vector carrying the gene encoding the carbonyl reductase variant, a genetically-engineered bacterium carrying the carbonyl reductase variant gene and glucose dehydrogenase gene, and an application of this bacterium in the asymmetric reduction of 4-chloroacetoacetate to prepare (R)-4-chloro-3-hydroxybutyrate.

11 Claims, 2 Drawing Sheets

Specification includes a Sequence Listing.

SEQUENCE LISTING

```
<160> NUMBER OF SEQ ID NOS: 4

<210> SEQ ID NO 1
<211> LENGTH: 34
<212> TYPE: DNA
<213> ORGANISM: Artificial Sequence
<220> FEATURE:
<223> OTHER INFORMATION: synthetic

<400> SEQUENCE: 1
ggcctctcca atgtgctttg atatcactga cagt                              34

<210> SEQ ID NO 2
<211> LENGTH: 34
<212> TYPE: DNA
<213> ORGANISM: Artificial Sequence
<220> FEATURE:
<223> OTHER INFORMATION: synthetic

<400> SEQUENCE: 2
tatcaaagca cattggagag gccgtatgta gaac                              34

<210> SEQ ID NO 3
<211> LENGTH: 1029
<212> TYPE: DNA
<213> ORGANISM: Artificial Sequence
<220> FEATURE:
<223> OTHER INFORMATION: synthetic

<400> SEQUENCE: 3
atgtcagttt tcgtttcagg tgctaacggg ttcattgccc aacacattgt cgatctcctg     60
ttgaaggaag actataaggt catcggttct gccagaagtc aagaaaaggc cgagaattta    120
acggaggcct ttggtaacaa cccaaaattc tccatggaag ttgtcccaga catatctaag    180
ctggacgcat tgaccatgt tttccaaaag cacggcaagg atatcaagat agttctacat    240
acggcctctc cattctgctt tgatatcact gacagtgaac gcgatttatt aattcctgct    300
gtgaacggtg ttaagggaat tctccactca attaaaaaat acgccgctga ttctgtagaa    360
cgtgtagttc tcacctcttc ttatgcagct gtgttcgata tggcaaaaga aaacgataag    420
tctttaacat ttaacgaaga atcctggaac ccagctacct gggagagttg ccaaagtgac    480
```

-continued

```
ccagttaacg cctactgtgg ttctaagaag tttgctgaaa aagcagcttg ggaatttcta      540
gaggagaata gagactctgt aaaattcgaa ttaactgccg ttaacccagt ttacgttttt      600
ggtccgcaaa tgtttgacaa agatgtgaaa aaacacttga acacatcttg cgaactcgtc      660
aacagcttga tgcatttatc accagaggac aagataccgg aactatttgg tggatacatt      720
gatgttcgtg atgttgcaaa ggctcattta gttgccttcc aaaagaggga acaattggt      780 caaagactaa tcgtatcgga ggccagattt actatgcagg atgttctcga tatccttaac      840
gaagacttcc ctgttctaaa aggcaatatt ccagtgggga accaggttc tggtgctacc      900 cataacaccc ttggtgctac tcttgataat aaaaagagta agaaattgtt aggtttcaag      960
ttcaggaact tgaaagagac cattgacgac actgcctccc aaatttttaaa atttgagggc     1020 agaatataa                                                              1029
```

<210> SEQ ID NO 4
<211> LENGTH: 342
<212> TYPE: PRT
<213> ORGANISM: Artificial Sequence
<220> FEATURE:
<223> OTHER INFORMATION: synthetic

<400> SEQUENCE: 4

```
Met Ser Val Phe Val Ser Gly Ala Asn Gly Phe Ile Ala Gln His Ile
1               5                   10                  15

Val Asp Leu Leu Leu Lys Glu Asp Tyr Lys Val Ile Gly Ser Ala Arg
            20                  25                  30

Ser Gln Glu Lys Ala Glu Asn Leu Thr Glu Ala Phe Gly Asn Asn Pro
        35                  40                  45

Lys Phe Ser Met Glu Val Val Pro Asp Ile Ser Lys Leu Asp Ala Phe
    50                  55                  60

Asp His Val Phe Gln Lys His Gly Lys Asp Ile Lys Ile Val Leu His
65                  70                  75                  80

Thr Ala Ser Pro Phe Cys Phe Asp Ile Thr Asp Ser Glu Arg Asp Leu
                85                  90                  95

Leu Ile Pro Ala Val Asn Gly Val Lys Gly Ile Leu His Ser Ile Lys
            100                 105                 110

Lys Tyr Ala Ala Asp Ser Val Glu Arg Val Val Leu Thr Ser Ser Tyr
        115                 120                 125

Ala Ala Val Phe Asp Met Ala Lys Glu Asn Asp Lys Ser Leu Thr Phe
    130                 135                 140

Asn Glu Glu Ser Trp Asn Pro Ala Thr Trp Glu Ser Cys Gln Ser Asp
145                 150                 155                 160

Pro Val Asn Ala Tyr Cys Gly Ser Lys Lys Phe Ala Glu Lys Ala Ala
                165                 170                 175

Trp Glu Phe Leu Glu Glu Asn Arg Asp Ser Val Lys Phe Glu Leu Thr
            180                 185                 190

Ala Val Asn Pro Val Tyr Val Phe Gly Pro Gln Met Phe Asp Lys Asp
        195                 200                 205

Val Lys Lys His Leu Asn Thr Ser Cys Glu Leu Val Asn Ser Leu Met
    210                 215                 220

His Leu Ser Pro Glu Asp Lys Ile Pro Glu Leu Phe Gly Gly Tyr Ile
225                 230                 235                 240

Asp Val Arg Asp Val Ala Lys Ala His Leu Val Ala Phe Gln Lys Arg
                245                 250                 255
```

-continued

| | | | | | | | | | | | | |
|---|---|---|---|---|---|---|---|---|---|---|---|---|
| Glu | Thr | Ile | Gly 260 | Gln | Arg | Leu | Ile | Val 265 | Ser | Glu | Ala | Arg | Phe 270 | Thr | Met |
| Gln | Asp | Val 275 | Leu | Asp | Ile | Leu | Asn 280 | Glu | Asp | Phe | Pro | Val 285 | Leu | Lys | Gly |
| Asn | Ile | Pro 290 | Val | Gly | Lys | Pro 295 | Gly | Ser | Gly | Ala | Thr 300 | His | Asn | Thr | Leu |
| Gly | Ala | Thr | Leu | Asp | Asn 310 | Lys | Lys | Ser | Lys | Lys 315 | Leu | Leu | Gly | Phe | Lys 320 |
| 305 | | | | | | | | | | | | | | | |
| Phe | Arg | Asn | Leu | Lys 325 | Glu | Thr | Ile | Asp | Asp 330 | Thr | Ala | Ser | Gln | Ile 335 | Leu |
| Lys | Phe | Glu | Gly | Arg 340 | Ile | | | | | | | | | | |

CARBONYL REDUCTASE VARIANT AND ITS USE IN PREPARATION OF (R)-4-CHLORO-3-HYDROXYBUTYRATE

REFERENCE TO AN ELECTRONIC SEQUENCE LISTING

The contents of the electronic sequence listing (Untitled ST25.txt; Size: 6,000 bytes; and Date of Creation: Aug. 17, 2020) is herein incorporated by reference in its entirety.

CROSS-REFERENCE TO RELATED APPLICATIONS

This application claims the benefit of priority from a Chinese Patent Application No. 202010121015.9, filed on Feb. 26, 2020. The content of the aforementioned application, including any intervening amendments thereto, is incorporated herein by reference in its entirety.

TECHNICAL FIELD

The present application relates to biopharmaceutics and bioengineering, and more particularly to a carbonyl reductase YOL151W variant and its encoding gene; genetically-engineered bacteria carrying the encoding gene of the carbonyl reductase variant and glucose dehydrogenase gene and a preparation method therefor; and a method for preparing (R)-4-chloro-3-hydroxybutyrate using the genetically-engineered bacteria under asymmetric reduction of chloroacetoacetate.

BACKGROUND (R)-4-chloro-3-hydroxybutyrate is an important class of chiral compounds, which is widely used in the synthesis of many valuable drugs and active molecules, such as a diet supplement L-carnitine (Chinese Patent No. 104726507; Journal of Shenyang University of Chemical Technology, 2017, 31, p 311-314). The biological asymmetric reduction of chloroacetoacetate is simple, efficient, highly selective, environmentally friendly and economical for the preparation of (R)-4-chloro-3-hydroxybutyrate. Kim and Sakai, et al. (J. Microbiol. Biotechnol., 2010, 20, 1300-1306; Tetrahedron, 2006, 62, 6143-6149) disclosed the catalytic reduction of ethyl 4-chloroacetoacetate using the carbonyl reductase YOL151W from *Saccharomyces cerevisiae* to prepare ethyl (R)-4-chloro-3-hydroxybutyrate, with an excellent enantioselectivity (97% ee). However, such process has an extremely low substrate concentration (≤10 g/L, mass percent concentration ≤1%), which limits its industrial application.

Until now, no report on the modification of YOL151W through site-directed mutagenesis based on protein structure information has been found to prepare an enzyme variant with enhanced reducing ability for 4-chloroacetoacetate and use such enzyme variant for the high substrate concentration synthesis of (R)-4-chloro-3-hydroxybutyrate.

SUMMARY

An object of this application is to provide a YOL151W variant with high catalytic activity to solve the problem of low substrate concentration in the catalytic reduction of 4-chloroacetoacetate using the wild-type carbonyl reductase YOL151W.

Correspondingly, this application also provides a nucleotide sequence encoding such variant and a recombinant expression vector comprising the nucleotide sequence. Moreover, this application further provides genetically-engineered bacteria carrying the nucleotide sequence encoding the carbonyl reductase variant and glucose dehydrogenase gene, a preparation method therefor, and a method for preparing (R)-4-chloro-3-hydroxybutyrate using the genetically-engineered bacteria under asymmetric reduction of chloroacetoacetate.

The technical solutions of this application are described as follows.

Specifically, the application provides a carbonyl reductase variant, which is obtained by:

(a) mutating phenylalanine-85 in an amino acid sequence as shown in SEQ ID NO:4 (wild-type carbonyl reductase YOL151W) to methionine.

The amino acid sequence (SEQ ID NO:4) of the wild-type carbonyl reductase YOL151W is shown as follows:

MSVFVSGANGFIAQHIVDLL
LKEDYKVIGSARSQEKAENL
TEAFGNNPKF SMEVVPDISK
LDAFDHVFQKHGKDIKIVLH
TASPFCFDITDSERDLLIPA
VNGVKGILHSIKKYAADSVE
RVVLTS SYAAVFDMAKENDK
SLTFNEESWNPATWESCQSD
PVNAYCGSKKFAEKAAWEFL
EENRDSVKFELTAVNPVYVF
GPQMFDKDVKKHLNTSCELV
NSLMHLSPEDKIPELFGGYI
DVRDVAKAHLVAFQKRETIG
QRLIVSEARFTMQDVLDILN
EDFPVLKGNIPVGKPGSGAT
HNTLGATLDNKKSKKLLGFK
FRNLKETIDDTASQILKFEG
RI

In an embodiment, a mutation of the carbonyl reductase variant further comprises a replacement of an amino acid at one or more positions other than position 85, on the premise of keeping enzyme catalytic activity, to obtain a protein derived from YOL151W and having the ability to reduce 4-chloroacetoacetate.

In an embodiment, the carbonyl reductase YOL151W variant is obtained by mutating phenylalanine-85 in the amino acid sequence of the wild-type carbonyl reductase YOL151W to methionine, and is thus named YOL151W$^{F85M}$.

In the present application, the nucleotide sequence encoding the wild-type carbonyl reductase YOL151W is shown in SEQ ID NO:3:

ATGTCAGTTTTCGTTTCAGGTGCTAACGGGTT-
CATTGCCCAACACATTGTCGATC TCCTGTT-
GAAGGAAGACTATAAGGT-
CATCGGTTCTGCCAGAAGTCAAGAAAAGGCC
GAGAATTTAACGGAGGCCTTTGGTAACAACC-
CAAAATTCTCCATGGAAGTTGTCCCA
GACATATCTAAGCTGGACGCATTTGACCATGTTTTC-
CAAAAGCACGGCAAGGATATC AAGATAGTTCTA-
CATACGGCCTCTCCATTCTGCTTTGATAT-
CACTGACAGTGAACGC
GATTTATTAATTCCTGCTGTGAACGGTGTTAAGG-
GAATTCTCCACTCAATTAAAAAA TACGCCGCTGAT-
TCTGTAGAACGTGTAGTTCTCACCTCTTCT-
TATGCAGCTGTGTTCG
ATATGGCAAAAGAAAACGATAAGTCTTTAACATT-
TAACGAAGAATCCTGGAACCCA GCTACCTGG-

GAGAGTTGCCAAAGTGACCCAGTTAACGCC-
TACTGTGGTTCTAAGAAG
TTTGCTGAAAAAGCAGCTTGGGAATTTCTAGAG-
GAGAATAGAGACTCTGTAAAATTC GAAT-
TAACTGCCGTTAACCCAGTT-
TACGTTTTTGGTCCGCAAATGTTTGACAAAGAT
GTGAAAAAACACTTGAACA-
CATCTTGCGAACTCGTCAACAGCTTGATGCATT-
TATCA CCAGAGGACAAGATACCGGAACTAT-
TTGGTGGATACATTGATGTTCGTGATGTTGCA
AAGGCTCATTTAGTTGCCTTCCAAAAGAGG-
GAAACAATTGGTCAAAGACTAATCGT ATCG-
GAGGCCAGATTTACTATGCAGGATGTTCTCGA-
TATCCTTAACGAAGACTTCCC
TGTTCTAAAAGGCAATATTCCAGTGGG-
GAAACCAGGTTCTGGTGCTACCCATAACAC
CCTTGGTGCTACTCTTGA-
TAATAAAAAGAGTAAGAAATTGTTAGGTTT-
CAAGTTCAG GAACTTGAAAGAGACCAT-
TGACGACACTGCCTCCCAAATTTTAAAATTTG
AGGGCA GAATATAA

The protein formed by the above amino acid sequence of variant YOL151W$^{F85M}$ is produced through the site-directed mutagenesis based on the structural information of YOL151W. The obtained variant YOL151W$^{F85M}$ has significantly-improved catalytic activity, and is further modified by replacing one or more of the other three amino acid residues in the catalytic active site, i.e. the tyrosine-128, the phenylalanine-132 and the valine-162, with other amino acid residues, to produce other variants, in which the reducing ability for 4-chloroacetoacetate are further enhanced.

In an embodiment, the tyrosine-128 is replaced with alanine, methionine, glycine, leucine, valine or isoleucine; the phenylalanine-132 is replaced with alanine, methionine, glycine, leucine, valine or isoleucine; and the valine-162 is replaced with alanine, methionine, glycine, leucine or isoleucine.

The carbonyl reductase variant provided herein can be obtained through steps of: 1) subjecting a mutation primer containing the base information of F85M mutation to PCR amplification using a recombinant vector pET28b-YOL151W carrying the wild-type carbonyl reductase YOL151W gene from Saccharomyces cerevisiae as template to produce a recombinant expression vector pET28b-YOL151W$^{F85M}$ carrying the gene of the variant YOL151W$^{F85M}$; and 2) further subjecting another mutation primer containing the base information of other mutation sites to PCR amplification using the recombinant expression vector pET28b-YOL151W$^{F85M}$ carrying the gene of the variant YOL151W$^{F85M}$ as template to produce a recombinant expression vector carrying the gene of the another variant.

The application also provides an isolated nucleic acid encoding any one of the above-mentioned carbonyl reductase variants.

The application also provides a recombinant expression vector comprising the nucleic acid.

The application also provides a genetically-engineered bacterium, which contains not only the recombinant expression vector of the present application, but also a recombinant expression vector carrying glucose dehydrogenase gene.

The genetically-engineered bacteria can be prepared through the step of co-transforming a recombinant expression vectors containing the mutation information, such as pET28b-YOL151W$^{F85M}$, and a recombinant expression vector pACYC-GDH carrying glucose dehydrogenase gene into the host microorganisms to obtain the genetically-engineered bacteria, where the host microorganisms are preferably Escherichia coli (E. Coli), and more preferably E. Coli BL21 (DE3). In an embodiment, the genetically-engineered bacteria of the application are constructed by co-transforming the above-mentioned two recombinant expression plasmids into E. coli BL21(DE3), which is accordingly named E. coli BL21(DE3)/pET28b-YOL151W$^{F85M}$/pACYC-GDH. The transformation can be implemented using a common method in this field, such as heat shock method and electrotransformation. In an embodiment, the transformation is completed using the heat shock method, where the heat shock is performed at 42° C. for 45 seconds.

Whole-cell biocatalyst can be obtained from the culture during the culturing of the above genetically-engineered bacteria E. coli BL21(DE3)/pET28b-YOL151W$^{F85M}$/pACYC-GDH. Specifically, the recombinant E. coli cells are inoculated to a LB medium containing kanamycin (25 μg/mL) and chloramphenicol (12.5 μg/mL) and cultured at 37° C. and 150-200 rpm. When the optical density OD$_{600}$ of the culture medium reaches 0.5-1.0, preferably 0.6, 0.05-1.0 mM, preferably 0.1 mM, of isopropyl-β-D-thiogalactoside (IPTG) is added for induction to obtain a genetically-engineered recombinant whole-cell biocatalyst with high-level expression of YOL151W$^{F85M}$, where the induction is performed at 18° C. for 18 h.

The genetically-engineered bacteria can be used as a catalyst in the reduction of 4-chloroacetoacetate to prepare (R)-4-chloro-3-hydroxybutyrate.

Correspondingly, the application also provides a method for preparing (R)-4-chloro-3-hydroxybutyrate, comprising:
reducing substrate 4-chloroacetoacetate (I) at 20-50° C., preferably 25-40° C., in an initial reaction system with pH of 6-10, preferably 6.5-7.5, to produce (R)-4-chloro-3-hydroxybutyrate (II), as shown in the following reaction scheme:

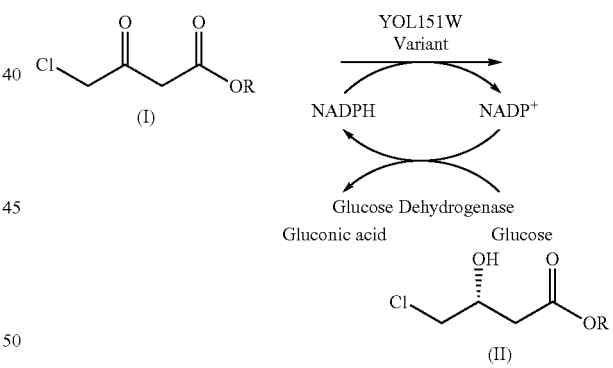

wherein:
R is linear or branched-chain $C_1$-$C_8$ alkyl, $C_3$-$C_8$ cycloalkyl, or mono-substituted or polysubstituted aryl or aralkyl;
the initial reaction system comprises the substrate 4-chloroacetoacetate (I), an enzyme catalyst, glucose, an organic solvent immiscible with water and a buffer solution; and
the enzyme catalyst is a whole cell of the genetically-engineered bacterium, or a crude enzyme obtained by the lysis of the whole cell of the genetically-engineered bacterium or an immobilized crude enzyme.

In an embodiment, based on a total volume of the initial reaction system, the substrate 4-chloroacetoacetate (I) has a concentration of 0.10-0.30 g/mL, preferably 0.10-0.25 g/mL; the organic solvent has a volume percentage of 5%-40%, preferably 15%-35%; the buffer solution has a volume percentage of 95%-60%, preferably 85%-65%; the enzyme catalyst calculated based on wet bacterial cells is 20%-200%, preferably 50%-200%, by weight of the substrate; and a molar ratio of the glucose to the substrate 4-chloroacetoacetate (I) is 1-4:1, preferably 1-2:1.

In an embodiment, the organic solvent is toluene.

In an embodiment, the buffer solution is phosphate buffered solution.

In an embodiment, in the preparation of (R)-4-chloro-3-hydroxybutyrate, the substrate 4-chloroacetoacetate (I) and the organic solvent are first added into the reaction vessel, and stirred uniformly at 20-50° C., and then the glucose and a uniform suspension of the enzyme catalyst in the buffer solution are added in sequence.

In an embodiment, an alkaline solution is added to keep the pH at 6-10, preferably 6.5-7.5, during the reaction, where the alkaline solution includes but is not limited to aqueous $K_2CO_3$ solution, aqueous $Na_2CO_3$ solution, aqueous $KHCO_3$ solution and aqueous $NaHCO_3$ solution.

In an embodiment, after the reaction is completed, the reaction mixture is subjected to post-treatment to a finished product, where the post-treatment includes the steps of:

(1) introducing ethyl acetate to the reaction mixture; stirring the reaction mixture for 4-10 min; and centrifuging the reaction mixture at 9,000-10,000 rpm for 15-30 min;

(2) collecting the organic phase obtained in step (1) and washing the aqueous phase three times with an equal volume of ethyl acetate followed by centrifugation at 9,000-10,000 rpm for 15-30 min to collect organic phases; and (3) combining the organic phases obtained in step (2); drying the combined organic phase with anhydrous sodium sulfate; and evaporating the combined organic phase under rotation to produce the finished product.

Compared to the wild-type carbonyl reductase, the carbonyl reductase variant provided herein has significantly improved ability to reduce 4-chloroacetoacetate. Moreover, the carbonyl reductase variant is suitable for the highly-stereoselective, green and economical synthesis of (R)-4-chloro-3-hydroxybutyrate in the presence of high concentration of the substrate, having good industrial application prospect.

DETAILED DESCRIPTION OF EMBODIMENTS

As used herein, the term "alkyl" refers to a linear or branched alkyl having 1-10 carbon atoms, preferably 1-8 carbon atoms, and more preferably 1-5 carbon atoms, such as methyl, ethyl, n-propyl, isopropyl, n-butyl, isobutyl, sec-butyl, tert-butyl, n-pentyl and n-hexyl.

In the application, the $C_3$-$C_8$ cycloalkyl includes, but is not limited to cyclopropyl, cyclobutyl, cyclopentyl and cyclohexyl.

As used herein, the term "aryl" refers to monocyclic, polycyclic or fused-ring aryl having 6-36 carbon atoms, preferably 6-14 carbon atoms, such as phenyl, naphthyl, anthryl, phenanthryl, biphenyl and binaphthyl. The aryl may be a mono-substituted or polysubstituted aryl, for example, the aryl can be substituted with one or more substituents, such as alkyl.

As used herein, the term "aralkyl" refers to an alkyl in which at least one hydrogen atom is substituted with aryl group, preferably a $C_7$-$C_{15}$ aralkyl, such as benzyl, 1-phenylethyl, 2-phenylethyl, 1-phenylpropyl and 3-naphthylpropyl, etc. The aryl group of the aralkyl can be mono-substituted or polysubstituted accordingly with one or more substituents, such as alkyl.

As used herein, the term "phenylalanine-85" refers to the phenylalanine at position 85. The application will be described in detail below with reference to the embodiments, but is not limited thereto.

Example 1 Site-Directed Mutagenesis and Construction of Recombinant Expression Vector pET28b-YOL151W$^{F85M}$ The site-directed mutagenesis was accomplished using the TransStartFastPfu Fly DNA polymerase. First, the mutation primers containing the mutation site F85M were designed as follows:

forward primer: GGCCTCTCCAATGTGCTTTGATAT-CACTGACAGT (SEQ ID NO:1);
reverse primer: TATCAAAGCACATTG-GAGAGGCCGTATGTAGAAC (SEQ ID NO:2);

The PCR reaction system had a total volume of 50 μL and consisted of 50 ng of wild-type pET28b-YOL151W template, 10 μL 5× TransStart®FastPfu Fly buffer solution, 8 μL dNTP (2.5 mM for each), a pair of the mutation primers each for 1 μL (10 μM), 10 μL of 5×PCR Stimulant, 2.5 U of TransStartFastPfu Fly DNA polymerase and sterile distilled water.

The PCR amplification was programmed as follows: denaturation at 98° C. for 3 min; 20 cycles with each consisting of denaturation at 98° C. for 20 seconds, annealing at 65° C. for 30 seconds and extension at 72° C. for 8 min; and extension at 72° C. for 10 min. The PCR product was stored at 4° C. for use.

The PCR product was digested by endonuclease DpnI at 37° C. for 1 h and then transformed into E. coli DH5 cells, which were smeared onto an LB solid medium containing kanamycin (50 μg/mL) and cultured overnight at 37° C. After that, positive clones were selected, inoculated into a LB medium containing kanamycin (50 μg/mL) and cultured for approximately 8 h. Plasmids were extracted and sequenced, and the plasmids with the correct sequence were the recombinant expression vector pET28b-YOL151W$^{F85M}$.

Example 2 Expression and Purification of pET28b-YOL151W$^{F85M}$

Figure 1:
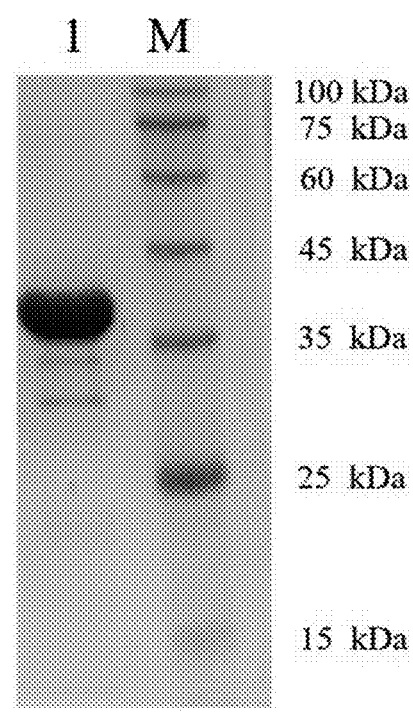
FIG. 1 is a SDS-PAGE electropherogram of a carbonyl reductase variant YOL151W$^{F85M}$ according to the present application, in which, M: marker; and 1: the purified carbonyl reductase variant YOL151W$^{F85M}$.

The recombinant expression vector pET28b-YOL151W$^{F85M}$ constructed in Example 1 was transformed into E. coli BL21 (DE3) cells. Monoclones were selected and inoculated to a LB liquid medium containing kanamycin (50 μg/mL) and activated for 8 h (37° C., 200 rpm). Then the activated culture was transferred to 500 mL of a LB liquid medium containing kanamycin (50 μg/mL) at an inoculation amount of 1/100 and cultured at 37° C. and 200 rpm. When the optical density $OD_{600}$ of the culture medium reached 0.6, 0.1 mM IPTG was added for induction, where the induction was performed at 18° C. and 200 rpm for 18 h. The culture medium was centrifuged, and wet bacterial cells (approximately 2 g) were collected and resuspended in 20 mL of a lysis buffer. The resuspension was mixed uniformly, ultrasonicated centrifuged at 4° C. and 18,000 rpm for 30 min to give a supernatant. The supernatant was loaded to a column containing 2-3 mL of Ni-NTA resin pretreated with the lysis buffer. The column was placed in an ice bath and subjected to oscillation on a horizontal oscillator for 30 min. The effluent was discarded, and the resin was washed with 2×20 mL of a washing buffer. The proteins bonded to the resin were eluted with an elution buffer, and 10 ingredients were collected, each for 1 mL. The ingredients were measured at 280 nm for the absorbance by spectrophotometer NanoDrop One, and those with high absorbance were combined. The combined protein solution was concentrated, allowed to flow through a PD-10 desalting column equilibrated with a storing buffer in advance and finally eluted with the storing buffer, and thus the purified YOL151W$^{F85M}$ variant without imidazole and excess salt was produced, which was demonstrated by SDS-PAGE to have a protein purity higher than 90% (shown in FIG. 1).

As used above, the lysis buffer was composed of 50 mM phosphate buffer (pH 7.5), 300 mM NaCl, 10 mM imidazole and 10% (v/v) glycerin;

the washing buffer was composed of 50 mM phosphate buffer (pH 7.5), 300 mM NaCl, 20 mM imidazole and 10% (v/v) glycerin;

the elution buffer was composed of 50 mM phosphate buffer (pH 7.5), 300 mM NaCl, 250 mM imidazole and 10% (v/v) glycerin; and the storing buffer was composed of 50 mM phosphate buffer (pH 7.5), 300 mM NaCl and 10% (v/v) glycerin.

Example 3 Construction of Genetically-Engineered Bacteria E. coli BL21(DE3)/pET28b-YOL151W$^{F85M}$/pACYC-GDH and Induced Expression of YOL151W$^{F85M}$ Gene The plasmid pET28b-YOL151W$^{F85M}$ constructed in Example 1 and the plasmid pACYC-GDH stored in the laboratory were together transformed into the expression host E. coli BL21(DE3), and positive clones were obtained through screening, and named E. coli BL21(DE3)/pET28b-YOL151W$^{F85M}$/pACYC-GDH. The genetically-engineered bacteria were inoculated to 5 mL of a LB liquid medium containing kanamycin (25 μg/mL) and chloramphenicol (12.5 μg/mL), activated for 8 h (37° C., 200 rpm). Then the activated culture was transferred to 500 mL of the LB liquid medium containing kanamycin (50 μg/mL) and chloramphenicol (12.5 μg/mL) at an inoculation of 1/100 and cultured at 37° C. and 200 rpm. When the optical density OD$_{600}$ of the culture medium reached 0.6, 0.1 mM IPTG was added for induction, where the induction was performed at 18° C. for 18 h. After the induction, the culture medium was centrifuged, and the wet bacterial cells were collected as the genetically-engineered bacteria whole-cell biocatalyst.

Example 4 Asymmetric Synthesis of ethyl (R)-4-chloro-3-hydroxybutyrate (Hectogram Scale) Under the Catalysis of Genetically-Engineered Bacteria E. coli BL21(DE3)/pET28b-YOL151WF85M/pACYC-GDH Whole Cell 346.8 g of ethyl 4-chloroacetoacetate (2.11 mol) was added into a reactor, to which toluene (534 mL) was added under stirring. The reactor was kept at 30° C. Then 570.9 g of glucose (3.17 mol) was added, and the reaction mixture was stirred for 5 min and added with a bacterial suspension, where the bacterial suspension was prepared by mixing 260 g of the whole-cell biocatalyst prepared in Example 3 with 1.2 L 100 mM phosphate buffered solution (pH 6.7) uniformly. After the reaction started, pH was monitored in real time and kept at 6.7 with 2 M aqueous K$_2$CO$_3$ solution.

After the reaction was monitored by GC-MS to be completed, the reaction mixture was added with 300 mL of ethyl acetate, stirred for 5 min and centrifuged at 9,500 rpm for 20 min. The organic phase was collected, and the aqueous phase was extracted with the equal volume of ethyl acetate three times and centrifuged at 9,500 rpm for 20 min to collect the organic phases. The organic phases were combined, dried with anhydrous sodium sulfate and evaporated under rotation to give 319.4 g of a product (91% yield) with a specific rotation of $[\alpha]^{25}_D$=+21.5 (c=5.0, CHCl$_3$) ($[\alpha]^{25}_D$=+22.3 (c=5.0, CHCl$_3$) in Org. Biomol. Chem., 2011, 9, 5463-5468).

$^1$H NMR (CDCl$_3$, 400 MHz): δ/ppm 4.31-4.25 (m, 1H), 4.18 (q, J=7.2 Hz, 2H), 3.63-3.58 (m, 2H), 3.15 (s, 1H), 2.68-2.61 (m, 2H), 1.30 (t, J=7.2 Hz, 3H).

$^{13}$C NMR (CDCl$_3$, 100 MHz): δ/ppm 172.0, 67.8, 60.6, 48.2, 38.7, 14.0.

The product ethyl (R)-4-chloro-3-hydroxybutyrate was derivatized to compound X-1 via the following reaction for the purpose of accurately determining an enantiomeric excess (ee) of the product.

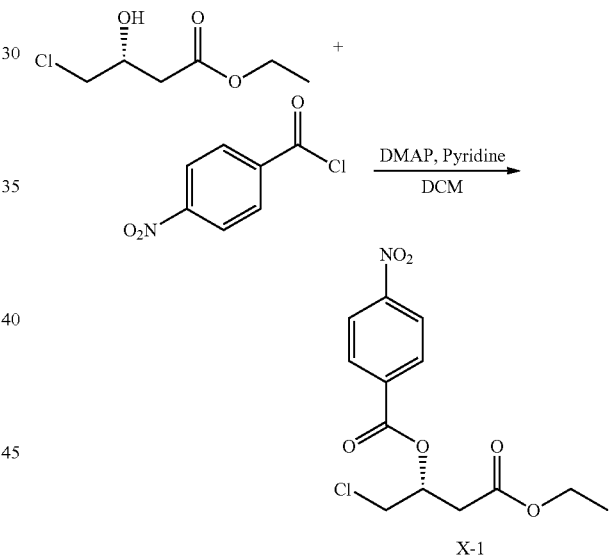

The derivatization was performed as follows. 10 mL of a dichloromethane solution containing 1 mmol of ethyl (R)-4-chloro-3-hydroxybutyrate, 5 mmol of pyridine, 1.5 mmol of 4-nitrobenzoyl chloride and 0.05 mmol of DMAP was stirred at 30° C. for 6 h. Then 5 mL of saturated aqueous sodium bicarbonate solution was added for extraction, and the reaction mixture was separated to obtain an organic layer. The organic layer was washed with 1 M hydrochloride solution, saturated aqueous sodium bicarbonate solution and saturated NaCl solution, respectively, dried with anhydrous Na$_2$SO$_4$ and concentrated to give a crude product. The crude product was purified by silica gel column chromatography (ethyl acetate:petroleum ether=1:3 (v/v)) to give 0.91 mmol of the compound X-1 (91% yield).

$^1$H NMR (CDCl$_3$, 400 MHz): δ/ppm 8.54-8.18 (m, 4H), 5.71 (m, 1H), 4.18 (q, J=7.2 Hz, 2H), 3.91 (qd, J=12.0, 4.5 Hz, 2H), 2.95 (d, J=6.6 Hz, 2H), 1.31 (t, J=7.2 Hz, 3H).

Figure 2A:
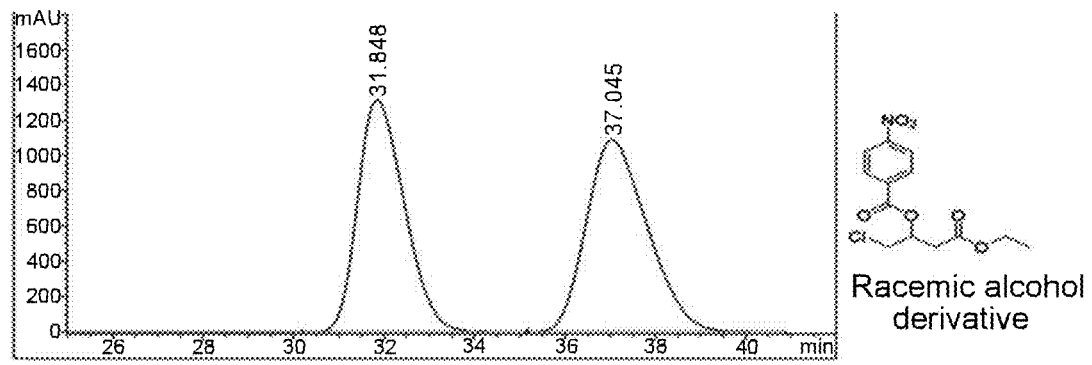
FIGS. 2A-B are HPLC maps of derivatives of ethyl (R)-4-chloro-3-hydroxybutyrate, in which, A is a HPLC map of a racemic alcohol derivative; and B is a chiral HPLC map of the purified ethyl (R)-4-chloro-3-hydroxybutyrate derivative according to Example 4 of the present application.
Figure 2B:
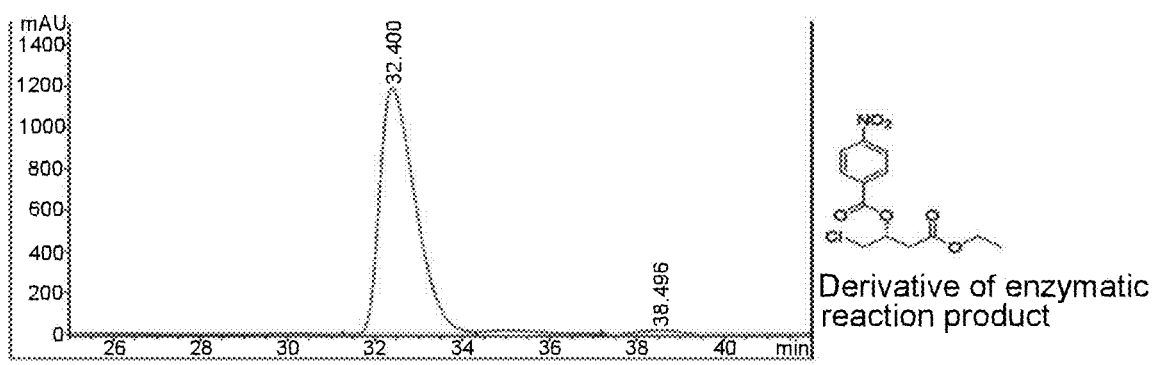

The chiral HPLC measurement was carried out under conditions of: AS-H chromatographic column; mobile phase: n-hexane:isopropanol=85:15; flow rate: 0.5 mL/min; column temperature 24° C.; and wavelength: 215 nm (shown in FIG. 2). The measurement result showed that an ee of the product was 97%.

Example 5 Asymmetric Synthesis of methyl (R)-4-chloro-3-hydroxybutyrate (Hectogram Scale) Under the Catalysis of Genetically-Engineered Bacteria *E. coli* BL21(DE3)/pET28b-YOL151WF85M/pACYC-GDH Whole Cell 115.6 g of methyl 4-chloroacetoacetate (0.77 mol) was added into a reactor, to which toluene (115 mL) was added under stirring. The reactor was kept at 30° C. Then 253.7 g of glucose (1.41 mol) was added, and the reaction mixture was stirred for 5 min and added with a bacterial suspension, where the bacterial suspension was prepared by mixing 115.6 g of whole-cell biocatalyst prepared in Example 3 with 463 mL of 100 mM phosphate buffered solution (pH 6.7) uniformly. After the reaction started, pH was monitored in real time and kept at 6.7 with 2M aqueous $K_2CO_3$ solution.

After the reaction was monitored by GC-MS to be completed, the reaction mixture was added with 100 mL of ethyl acetate, stirred for 5 min, and centrifuged at 9,500 rpm for 20 min. The organic phase was collected, and the aqueous phase was extracted with an equal volume of ethyl acetate three times and centrifuged at 9,500 rpm for 20 min to collect the organic phase. The organic phases were combined, dried with anhydrous sodium sulfate and evaporated under rotation to give 103.1 g of a product (88% yield).

$^1$H NMR (CDCl$_3$, 400 MHz): δ/ppm 4.31-4.24 (m, 1H), 3.73 (s, 3H), 3.64-3.57 (m, 2H), 3.06 (s, 1H), 2.68-2.61 (m, 2H).

$^{13}$C NMR (CDCl$_3$, 100 MHz): δ/ppm 172.1, 67.7, 51.9, 48.3, 38.3.

The product ethyl (R)-4-chloro-3-hydroxybutyrate was derivatized to compound X-2 via the following reaction for the purpose of accurately determining an ee of the product.

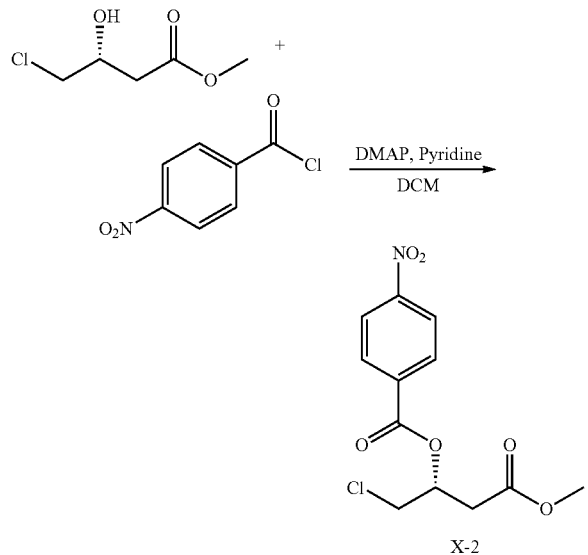

X-2

The derivatization was performed as follows. 10 mL of a dichloromethane solution containing 1 mmol of methyl (R)-4-chloro-3-hydroxybutyrate, 5 mmol of pyridine, 1.5 mmol of 4-nitrobenzoyl chloride and 0.05 mmol of DMAP was stirred at 30° C. for 6 h. Then 5 mL of saturated aqueous sodium bicarbonate solution was added for extraction and the reaction mixture was separated to obtain an organic layer. The organic layer was washed with 1 M hydrochloride solution, saturated aqueous sodium bicarbonate solution, and saturated NaCl solution, respectively, dried with anhydrous Na$_2$SO$_4$ and concentrated to give a crude product. The crude product was purified by silica gel column chromatography (ethyl acetate:petroleum ether=1:3 (v/v)), to give 0.93 mmol of the compound X-2 (93% yield).

$^1$H NMR (CDCl$_3$, 400 MHz): δ/ppm 8.52-8.17 (m, 4H), 5.73 (m, 1H), 3.93 (qd, J=12.0, 4.8 Hz, 2H), 3.74 (s, 3H), 2.94 (d, J=6.8 Hz, 2H).

The chiral HPLC measurement was carried out under conditions of: AS-H chromatographic column; mobile phase: n-hexane:isopropanol=85:15 solution; flow rate: 0.5 mL/min; column temperature 24° C.; and wavelength: 215 nm. The measurement result showed that an ee of the product was 98%.

Example 6 Asymmetric Synthesis of tert-butyl (R)-chloro-3-hydroxybutyrate (Hectogram Scale) Under the Catalysis of Genetically-Engineered Bacteria *E. coli* BL21(DE3)/pET28b-YOL151WF85M/pACYC-GDH Whole Cell 173.4 g of tert-butyl 4-chloroacetoacetate (0.90 mol) was added into a reactor, to which toluene (534 mL) was added under stirring. The reactor was kept at 30° C. Then 325.1 g of glucose (1.8 mol) was added, and the reaction mixture was stirred for 5 min and added with a bacterial suspension, where the bacterial suspension was prepared by mixing 346.8 g of whole-cell biocatalyst prepared in Example 3 with 1.2 L of 100 mM phosphate buffered solution (pH 6.7) uniformly. After the reaction started, pH was monitored in real time and kept at 6.7 with 2 M aqueous $K_2CO_3$ solution.

After the reaction was monitored by GC-MS to be completed, the reaction mixture was added with 600 mL of ethyl acetate, stirred for 5 min and centrifuged at 9,500 rpm for 20 min to collect an organic phase. The aqueous phase was extracted with an equal volume of ethyl acetate three times and centrifuged at 9,500 rpm for 20 min to collect the organic phases. The organic phases were combined, dried with anhydrous sodium sulfate and evaporated under rotation to give 157.7 g of a product (90% yield).

$^1$H NMR (CDCl$_3$, 400 MHz): δ/ppm 4.30-4.23 (m, 1H), 3.66-3.58 (m, 2H), 3.08 (s, 1H), 2.68-2.61 (m, 2H), 1.29 (s, 9H).

$^{13}$C NMR (CDCl$_3$, 100 MHz): δ/ppm 173.0, 82.1, 69.5, 51.5, 38.6, 28.8.

The product tert-butyl (R)-4-chloro-3-hydroxybutyrate was derivatized to compound X-3 via the following reaction for the purpose of accurately determining an ee of the product.

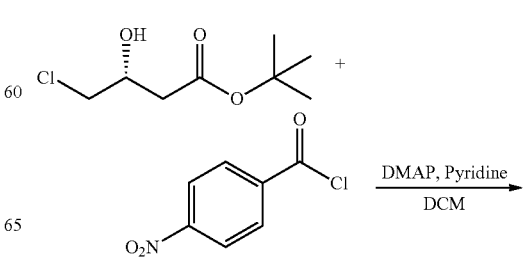

-continued

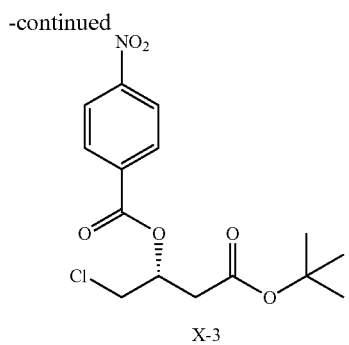

X-3

The derivatization was performed as follows. 10 mL of a dichloromethane solution containing 1 mmol of tert-butyl (R)-4-chloro-3-hydroxybutyrate, 5 mmol of pyridine, 1.5 mmol of 4-nitrobenzoyl chloride and 0.05 mmol of DMAP was stirred at 30° C. for 6 h. Then 5 mL of saturated aqueous sodium bicarbonate solution was added for extraction, and the reaction mixture was separated to obtain an organic layer. The organic layer was washed with 1 M hydrochloride solution, saturated aqueous sodium bicarbonate solution and saturated NaCl solution, respectively, dried with anhydrous $Na_2SO_4$ and concentrated to give a crude product. The crude product was purified by silica gel column chromatography (ethyl acetate:petroleum ether=1:3 (v/v)) to give 0.88 mmol of compound X-3 (88% yield).

$^1$H NMR (CDCl$_3$, 400 MHz): δ/ppm 8.53-8.17 (m, 4H), 5.70 (m, 1H), 3.89 (qd, J=11.8, 4.8 Hz, 2H), 2.92 (d, J=6.6 Hz, 2H), 1.31 (s, 9H)

Chiral HPLC measurement was carried out under conditions of: AS-H chromatographic column; mobile phase: n-hexane:isopropanol=85:15; flow rate: 0.5 mL/min; column temperature: 24° C.; and wavelength: 215 nm. The measurement result showed that an ee of the product was 97%.

Described above are merely preferred embodiments of the present application, which are merely illustrative of the present invention without limiting. Any changes, replacements and modifications made without departing from the spirit of the present application should fall within the scope as defined by the appended claims.

What is claimed is:

1. A carbonyl reductase variant, wherein the carbonyl reductase variant is obtained by:
   mutating phenylalanine-85 in the amino acid sequence as shown in SEQ ID NO:4 to methionine.

2. A carbonyl reductase variant, wherein the carbonyl reductase variant is obtained by:
   mutating phenylalanine-85 in the amino acid sequence as shown in SEQ ID NO:4 to methionine; and
   replacing an amino acid at one or more positions other than position 85 in the amino acid sequence as shown in SEQ ID NO: 4; wherein the amino acid at one or more positions is tyrosine-128, phenylalanine-132 or valine-162, or a combination thereof.

3. The carbonyl reductase variant of claim 2, wherein the tyrosine-128 is replaced with alanine, methionine, glycine, leucine, valine or isoleucine; the phenylalanine-132 is replaced with alanine, methionine, glycine, leucine, valine or isoleucine; and the valine-162 is replaced with alanine, methionine, glycine, leucine or isoleucine.

4. An isolated nucleic acid encoding the carbonyl reductase variant of claim 1.

5. A recombinant expression vector comprising the nucleic acid of claim 4.

6. A genetically-engineered bacterium, comprising:
   the recombinant expression vector of claim 5; and
   a recombinant expression vector carrying glucose dehydrogenase gene.

7. A method for preparing (R)-4-chloro-3-hydroxybutyrate, comprising:
   reducing substrate 4-chloroacetoacetate (I) at 20-50° C. in an initial reaction system at pH of 6-10 to produce the (R)-4-chloro-3-hydroxybutyrate (II), as shown in the following reaction scheme:

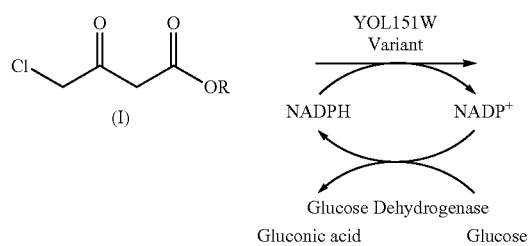

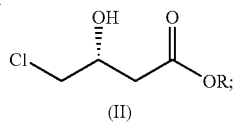

wherein:

R is a linear or branched-chain $C_1$-$C_8$ alkyl, a $C_3$-$C_8$ cycloalkyl, or a mono-substituted or poly-substituted aryl or aralkyl;

the initial reaction system comprises the substrate 4-chloroacetoacetate (I), an enzyme catalyst, glucose, an organic solvent immiscible with water and a buffer solution; and the enzyme catalyst is a whole cell of the genetically-engineered bacterium of claim 6, or a crude enzyme obtained by the lysis of the whole cell of the genetically-engineered bacterium.

8. The method of claim 7, wherein, based on a total volume of the initial reaction system, the substrate 4-chloroacetoacetate (I) has a concentration of 0.10-0.30 g/mL; the organic solvent has a volume percentage of 5%-40%; the buffer solution has a volume percentage of 95%-60%; the enzyme catalyst calculated as wet bacterial cells is 20%-200% by weight of the substrate 4-chloroacetoacetate (I); and a molar ratio of the glucose to the substrate 4-chloroacetoacetate (I) is 1-4:1.

9. The method of claim 7, wherein the organic solvent is toluene.

10. The method of claim 7, wherein the buffer solution is phosphate buffered solution.

11. The method of claim 7, wherein an alkaline solution is added to keep the pH at 6-10 during the reaction.

* * * * *